United States Patent
Stern (10) Patent No.: US 9,629,640 B2
(45) Date of Patent: Apr. 25, 2017

(54) QUICK-ACTION COUPLING

(71) Applicant: AESCULAP AG, Tuttlingen (DE)

(72) Inventor: Andreas Stern, Mönchweiler (DE)

(73) Assignee: AESCULAP AG, Tuttlingen (DE)

( * ) Notice: Subject to any disclaimer, the term of this patent is extended or adjusted under 35 U.S.C. 154(b) by 131 days.

(21) Appl. No.: 14/399,120

(22) PCT Filed: May 3, 2013

(86) PCT No.: PCT/EP2013/059293
§ 371 (c)(1),
(2) Date: Nov. 5, 2014

(87) PCT Pub. No.: WO2013/167496
PCT Pub. Date: Nov. 14, 2013

(65) Prior Publication Data
US 2015/0123357 A1    May 7, 2015

(30) Foreign Application Priority Data
May 8, 2012    (DE) .................. 10 2012 207 651

(51) Int. Cl.
*B23B 31/107*    (2006.01)
*A61B 17/16*    (2006.01)

(52) U.S. Cl.
CPC ........ *A61B 17/162* (2013.01); *B23B 31/1071* (2013.01); *B23B 2240/04* (2013.01);
(Continued)

(58) Field of Classification Search
CPC .............. A61B 17/162; B23B 31/1071; B23B 2240/04; Y10T 279/17777
See application file for complete search history.

(56) References Cited

U.S. PATENT DOCUMENTS 1,965,917 A  *  7/1934  Anderholm ......... B25B 23/0042
                                                    279/78
2,854,238 A  *  9/1958  Kennell .................. B21J 15/30
                                                    279/19.5
(Continued)

FOREIGN PATENT DOCUMENTS

EP           0 056 266 A1    7/1982

OTHER PUBLICATIONS

International Search Report for PCT/EP2013/059293 dated Oct. 24, 2013.

*Primary Examiner* — Eric A Gates
*Assistant Examiner* — Paul M Janeski
(74) *Attorney, Agent, or Firm* — Kenealy Vaidya LLP (57) ABSTRACT

The present application discloses a quick-action coupling (100) for a rotary surgical tool having a rotary shaft (20), in the distal end surface of which there is formed a tool receptacle (24) which is adapted to receive a rotary surgical tool for conjoint rotation. The rotary shaft (20) has, in the region of its distal end (21), at least one radial protrusion (22) and at least one radial aperture, wherein a locking body is arranged in the at least one aperture, said locking body being movable in the radial direction with respect to the rotary shaft (20). A sleeve (10), the proximal end of which is pushable over the distal end (21) of the rotary shaft (20), is additionally provided in the quick-action coupling. The inner surface of the sleeve (10) contains a region in which the inside diameter of the distal section (102) is enlarged compared with the inside diameter of the proximal section (101), and the sleeve (10) has at least one slot (11, 11', 12, 12', 13, 13', 13", 14, 15, 16, 17) which has a first slot section (11, 11') and at least one further slot section (12, 12', 13, 13', 13", 14, 15, 16, 17), wherein the first slot section (11, 11') extends from the proximal end of the sleeve (10) and the further slot section (12, 12', 13, 13', 13", 14, 15, 16, 17) is
(Continued)

connected to the first slot section (11, 11'). An elastic element (30) urges the sleeve (10) in the distal direction relative to the rotary shaft (20).

17 Claims, 5 Drawing Sheets

(52) U.S. Cl.
   CPC ............... *F04C 2270/0421* (2013.01); *Y10T 279/17752* (2015.01); *Y10T 279/17777* (2015.01); *Y10T 279/17811* (2015.01)

(56) References Cited

U.S. PATENT DOCUMENTS

| | | |
|---|---|---|
| 3,367,727 A | 2/1968 | Ward et al. |
| 4,954,025 A * | 9/1990 | Crawford .............. B25B 21/007 |
| | | 408/238 |
| 5,013,194 A | 5/1991 | Wienhold |
| 5,222,848 A | 6/1993 | Kuang-Wu |
| 6,179,302 B1 * | 1/2001 | Gauthier ............. B23B 31/1071 |
| | | 279/75 |
| 2007/0264093 A1 | 11/2007 | White et al. |
| 2009/0051129 A1 * | 2/2009 | Haas .................... B25D 17/088 |
| | | 279/146 |

* cited by examiner

QUICK-ACTION COUPLING

The present invention relates to a quick-action coupling for a rotary surgical tool, for example a bone drill or a bone cutter.

In operations performed on the bones of a patient, it is often necessary to drill or cut a bone. The rotary tool that is used to do this often has to be changed during the operation (OP), either as a result of wear or because a drill with a different diameter or a cutter with a different surface is intended to be used. In the field of surgical operations there is considerable pressure to reduce costs, and it is therefore important that tools can be changed quickly and safely. If there is a delay in changing tools, this not only affects the person operating the device but also all the other members of staff in the operating theater, since they then have to wait on the person operating the device.

However, far greater demands are placed on tools in the clinical sector than are placed on comparable tools, for example in the construction sector. Although tools have to be safe to operate in all environments, it is not a problem on a building site if, when inserting a drill into a coupling, the drill first of all drops to the ground. Sterility has to be ensured at all times in the clinical sector, and therefore a tool that drops to the floor or ends up in an area not considered to be sterile (usually all the surfaces and areas located under an operating table) has to be replaced by a sterile tool. This leads to delays in the conduct of the operation and to increased costs in re-conditioning the tools, since both tools then have to cleaned and sterilized after the operation.

In addition, the tool holder must also be able to be cleaned and sterilized in order to permit repeat use. Here, the tool holder is the drilling machine or the cutting machine, for example. Since the coupling is a part of the tool holder, it too must be suitable for cleaning and sterilizing. To this end, further demands may be placed on the tool coupling.

PRIOR ART

European patent application EP 0 056 266 A1 discloses a quick-release chuck. This quick-release chuck has a rotary shaft, in the distal end of which a tool receptacle is formed which, together with a tool that is to be inserted, produces a form-fit engagement, such that the tool is not rotatable in the tool receptacle. For this purpose, the receiving areas for the tools are normally hexagonal. A mushroom-shaped locking body is received in a radial aperture of the jacket surface of the tool receptacle and is pre-tensioned toward the rotation axis of the tool receptacle, such that, when a tool is inserted into the receptacle, the locking body enters a circumferential groove formed on the tool. The position of the locking body is secured by a rotatable sleeve, which is pre-tensioned by a spring, such that the tool is held fixedly in the tool receptacle as long as the sleeve is not turned to an open position counter to the pre-tensioning of the spring. However, this quick-release chuck is composed of a large number of structural parts which, after they have been assembled, are connected to one another such that they cannot be dismantled. Moreover, several hollow spaces (e.g. spring housing) and slots are formed in which tissue parts and body fluids could collect and which cannot be safely cleaned and sterilized in the context of a clinical sterilization procedure. Therefore, this quick-release chuck is in no way suitable for a rotary surgical tool.

U.S. Pat. No. 5,013,194 discloses a tool chuck which likewise can receive a hexagonal rear end of a tool provided with a circumferential groove. This tool has two balls as locking bodies which, in the locking position, bear on a protruding inner surface of a movable sleeve. In the release position of the sleeve, the balls can enter an annular space formed in the sleeve. A spring, which pre-tensions the sleeve in the locking position, is arranged in a second annular space in the sleeve. The spring is supported on a side wall of the supporting projection and on a retainer ring, which engages in a groove of the rotary shaft. Again, this tool chuck cannot be dismantled and therefore cannot be sterilized. A tool chuck of this kind cannot be used for a rotary surgical tool.

SUMMARY OF THE INVENTION AND DETAILED DESCRIPTION

The object of the present invention is therefore to make available a quick-action coupling which can be actuated quickly, easily and safely and which is additionally suitable for a clinical cleaning and sterilizing procedure. A further object of the present invention is to make available a tool holder having a quick-action coupling of this kind.

The object of the present invention is achieved by a quick-action coupling as claimed in claim 1. Advantageous developments of the invention are the subject matter of the dependent claims.

According to one aspect of the present invention, a quick-action coupling for a rotary surgical tool is made available, having a rotary shaft, in the distal end surface of which there is formed a tool receptacle. This receptacle is adapted to receive a rotary surgical tool for conjoint rotation therewith. This is usually achieved by means of the rear end of the tool and, correspondingly, the inner wall surface of the receptacle being configured with a polygonal and preferably hexagonal cross section. The rotary shaft has, in the area of its distal end, at least one radial projection and at least one radial aperture, wherein a locking body is arranged in the at least one aperture. The locking body is held movably in the radial direction with respect to the rotary shaft.

The quick-action coupling moreover has a sleeve, the proximal end of which is able to be pushed over the distal end of the rotary shaft. The inner surface of the sleeve has an area in which the internal diameter of the proximal portion is smaller than the internal diameter of the distal portion. Moreover, the inner surface of the sleeve can have further areas which, for example, form a bearing surface for the elastic element mentioned below, but the area defined here is adapted to come to bear on the at least one locking body during a movement in the distal direction and to urge the locking body toward the axis of the rotary shaft. In the case of an opposite movement of the sleeve in the proximal direction, the at least one locking body is freed, such that it can move radially outward at least to the extent that its inner end emerges from the tool receptacle. The sleeve has at least one slot which has a first slot portion and at least one further slot portion, wherein the first slot portion extends from the proximal end of the sleeve, and the further slot portion is connected to the first slot portion. The further slot portion preferably forms an angle α of at least 90° with the first slot portion. The further slot portion can be the second, third or also another slot portion and can even be composed of several of these slot portions. The fact that the first slot portion extends from the proximal end of the sleeve means that it is open toward the proximal end of the sleeve, such that the associated projection on the rotary shaft can be inserted into this slot from the direction of the proximal end of the sleeve. The slot can also be configured as a groove provided on the inner wall of the sleeve, such that the slot and the individual slot portions are not discernible from the outside. In addition, the quick-action coupling has an elastic element which urges the sleeve in the distal direction relative to the rotary shaft.

With such a configuration of the quick-action coupling, it is possible to dismantle the quick-action coupling into at least two individual parts, namely the sleeve and the tool receptacle, in which case the elastic element can either be part of one of the two other parts, or can be mounted fixedly on one of the two other parts, or can be provided as an individual third structural part. In this way, the quick-action coupling can be easily and quickly dismantled for cleaning and sterilizing and then reassembled, such that, during the cleaning and sterilizing, the quick-action coupling has no hollow spaces or narrow slits that are difficult to clean and sterilize. At the same time, the number of structural parts is reduced to the maximum extent, and there is therefore no need for complicated assembly and disassembly. In addition to this, no tool of any kind is required for the assembly and disassembly.

According to an advantageous development of the present invention, provision can be made that the further slot portion forms an angle of at least 90° with the first slot portion. In this case, the sleeve must be rotated at least counter to the frictional force about its axis, which is formed between further slot portion and lateral projection on the tool receptacle and which is caused by the elastic element, in order to reach a position in which the sleeve is removable from the tool receptacle. At an angle of more than 90°, the elastic element must also be pushed together to ensure that the sleeve is able to turn about its axis.

According to an advantageous embodiment of the present invention, the elastic element is a helical spring which is arranged about the rotary shaft. Advantageously, this spring is completely covered by the sleeve in the assembled state. Helical springs are known structural parts in surgical devices, and there can therefore be no doubt as to the helical springs being able to be cleaned and sterilized. In addition, enough suitable materials are known for making such a helical spring. By arranging the helical spring outside the tool receptacle, the length of the quick-action coupling can be minimized. If the spring were arranged in the interior of the tool receptacle, which is possible in principle, the area of the tool receptacle responsible for the form-fit engagement with the tool would have to be arranged proximally in relation to the area in which the spring is arranged. With the helical spring arranged on the outside, the helical spring and the form-fit engagement with the tool can be present in the same axial area.

According to another advantageous embodiment of the present invention, a bearing surface for the elastic element is formed on the sleeve and/or on the rotary shaft. Alternatively to this, the elastic element can also be designed such that it is pressed onto the outer surface of the tool receptacle. The force that the elastic element has to apply to the sleeve is not very great. Were the elastic element pressed onto the outer surface of the tool receptacle, this would still be possible without a tool, and the elastic element would also be able to be removed again from the tool receptacle without a tool. It is better, however, if a bearing surface is provided on the tool receptacle, such that the elastic element is able to detach itself almost free of force from the tool receptacle. Alternatively, the elastic element can be attached fixedly to the tool receptacle, e.g. by being welded on. In this case, the elastic element cannot detach from the tool receptacle, and therefore it cannot be lost.

According to yet another advantageous embodiment of the present invention, the locking body is a ball, and the aperture has, on both sides, a diameter that is smaller compared to a portion lying between said sides. A ball is especially suitable as a locking body, firstly because it can be installed in any desired position, which makes installation easier, and secondly because it is able to rotate in the aperture, which reduces the friction when a tool is inserted into the tool receptacle and so comes into contact with the locking body. The latter also applies to the contact between locking body and bearing surface in the sleeve, i.e. the area of the inner surface of the sleeve at which the diameter is reduced. Alternatively, a cylindrical, conical or mushroom-shaped locking body can also be provided. However, it does not have to be a rotationally symmetrical body. Nonetheless, the locking body is preferably rotationally symmetrical and, as is the case of the ball in particular, is provided with a rounded surface on both sides, i.e. toward the tool and toward the bearing surface.

According to another advantageous embodiment of the present invention, the first slot portion extends substantially in the distal direction and, at its distal end, this first slot portion is connected to the second slot portion, which extends substantially in the radial direction. The underlying principle of the various slot portions will be dealt with here first of all.

The slot portions together have to fulfill three different tasks, namely (1) forming the access for the pin, (2) securing the quick-action coupling against accidental dismantling, and (3) ensuring a movement of the sleeve between the release position and the locking position for the inserted tool. In addition to this, it is possible to fulfill the task (4) of temporarily immobilizing the sleeve in the release position and/or the locking position. These three or four tasks are fulfilled overall by the different slot portions, wherein one slot portion can also fulfill several tasks jointly and one task can extend to several slot portions. However, task (1) is always fulfilled by the first slot portion, since the first slot portion is defined as the slot portion that is open toward the proximal end of the sleeve. It is important here that task (1) and task (3) are not undertaken by the same slot portion, since it is not then possible to ensure that the quick-action coupling is not inadvertently dismantled. Task (2) can be fulfilled by a dedicated slot portion or by a slot portion which, on its own or together with another slot portion, fulfills task (1) or (3) and/or optionally also task (4).

The direction indicators used are explained below. The distal direction is the direction toward the tool tip and is counter to the proximal direction, which extends toward the tool holder. The radial direction is at right angles to the proximal and distal directions and extends along the circumference of the tool receptacle and the sleeve. The radial direction generally designates both possible circumferential directions. The contra-radial direction is the radial direction which is diametrically opposite to a previously stated direction, i.e. in the reverse direction of rotation as it were. If a slot portion extends radially and distally or proximally, it then extends obliquely along the sleeve. All the direction indicators relate to the main direction and allow for slight deviations that do not affect functionality. In the case of slots that are bent or curved, the direction is the shortest connection between both ends of a slot portion on the jacket surface of the sleeve. As a result of the cylinder shape of the sleeve, all slots are curved except for the slots that extend purely distally or proximally. However, this is not intended to be described by the term curved slots or bent slots. Instead, these terms stand for slots which have a curvature or bend even when the jacket surface of the sleeve is rolled out on a plane. Accordingly, multi-dimensionally curved or bent slots can also be provided. Moreover, the slot portions can also be step-shaped, i.e. they can be composed of distal/proximal and radial/contra-radial portions.

In accordance with the aforementioned design of the quick-action coupling sleeve, there are numerous possible arrangements and corresponding distributions of tasks for the individual slot portions, which however fulfill all tasks (1) to (3) together and thus form a functional quick-action coupling.

According to yet another advantageous embodiment of the present invention, the first slot portion extends obliquely in the distal and radial direction and, at its distal end, is connected to the second slot portion. The first slot portion here fulfills tasks (1) and (2), and the second slot portion fulfills task (3). Release or locking of the tool (task (1)) in the tool receptacle is effected here by the second slot portion, and dismantling and assembly (task (3)) by the first slot portion. Securing against inadvertent dismantling (task (2)) is likewise effected here by the first slot portion. To permit dismantling and assembly, the sleeve has to be rotated in each case and at the same time pushed in the distal direction. Depending on the friction and strength of the elastic element, the movement of the sleeve in the distal direction can also be undertaken by the elastic element. If the third slot portion is step-shaped, it is possible, for example, to prevent the tool being accidentally released when the sleeve comes into contact with an object, for example tissue. By simple pushing in the proximal direction, the sleeve can be brought from the locking position only to an intermediate position, from where a radial rotation is first of all needed in order then to have the possibility of bringing the sleeve to the release position, by pushing it further in the proximal direction, or of dismantling the coupling by further radial rotation and subsequent distal movement.

According to yet another advantageous embodiment of the present invention, a radial step is formed in the first slot portion, near the proximal edge of the sleeve. This step is provided in order to prevent a situation where, as a result of the pre-tensioning of the elastic element, the sleeve springs away from the tool receptacle if the sleeve is accidentally let go during assembly or disassembly. A first slot portion designed in this way has the effect that, if the sleeve is accidentally let go during assembly or disassembly while the projection is located in the distal direction from the radial step in the first slot portion, the projection strikes against the radial step and remains in contact there. The elastic element can moreover be configured such that, in this position, only a very slight pre-tensioning is still applied to the sleeve, with the result that, when the projection is located in the proximal direction from the radial step, this remaining pre-tensioning is no longer sufficient to allow the sleeve to spring away from the tool receptacle.

According to another advantageous embodiment of the present invention, two or three slots are provided on a sleeve and are arranged at uniform angular intervals along the circumferential direction of the sleeve. Accordingly, an equal number of radial projections are formed on the rotary shaft and are arranged correspondingly. Each projection thus runs in a slot. Since the slots and projections are arranged at uniform angular intervals, there is no wrong arrangement of the sleeve with respect to the tool receptacle, as long as only a single projection is received in a slot. As an alternative to this, it is possible to use angular intervals that are not uniform, for example in order to ensure the assignment of specific sleeves to specific tool receptacles.

According to another advantageous embodiment of the present invention, two or three radial apertures are formed in the side wall of the tool receptacle and a ball is arranged as a locking body in each aperture. This ball is held in the aperture by means of at least one part of at least one edge of the aperture being plastically deformed toward the hole center. In order to minimize the friction between edge and ball, it is expedient if at least almost the entire edge along the circumferential limit of the aperture is plastically deformed toward the center of the aperture. The plastic deformation is obtained for example by a hollow cylindrical punch, which has a slightly larger diameter than the aperture and is pressed concentrically with respect to the aperture, into the surface of the tool receptacle. Since this principle is difficult to implement on the inside width of the aperture for reasons of space, the ball can be held toward the inside in the aperture, by means of the aperture being drilled, wherein either a small through-hole is firstly drilled and then a concentric and slightly larger blind hole, or by a drill which has a smaller diameter in the area of its tip. In principle, the aperture can also be provided on one side or on both sides with a thread, into which a constriction ring is screwed which reduces the diameter of the opening of the aperture. Such a constriction ring can also be introduced some other way into the aperture and be fixed or it can be mounted on the sleeve.

According to another advantageous embodiment of the present invention, a step or an inclined surface is provided in the area of the inner surface of the sleeve between the proximal portion and the distal portion. A step has the advantage that only a very short travel of the sleeve in the distal/proximal direction is needed to get from the release position to the locking position of the quick-action coupling. An inclined surface has the advantage that no force peak occurs during the movement and the sleeve does not briefly stick when the step bears on the one or more locking elements from the lateral (i.e. axial) direction. Other shapes of the bearing surface are likewise possible. For example, the bearing surface can have multiple steps or a paraboloid or hyperboloid shape.

According to another advantageous embodiment of the present invention, the slot is configured in such a way that it extends through the entire wall thickness of the sleeve. In principle, the at least one slot may also be designed as a groove, which is formed on the inner surface of the sleeve. However, this has the disadvantage that the profile of the slot portions is not discernible to the user, such that handling of the quick-action coupling is made more difficult. Nonetheless, this disadvantage can be overcome if the profile of the slot portions is indicated graphically or drawn on the outside of the sleeve. This has the advantage that the user does not touch the slot portions and in particular the edges thereof.

According to another advantageous embodiment of the present invention, the rotary surgical tool is in particular a drill or a cutter. However, the present invention can also be used for all other rotary tools.

Further advantages and features of the invention will be clear to a person skilled in the art from the attached figures and from the detailed description of the illustrative embodiments.

Figure 3A:
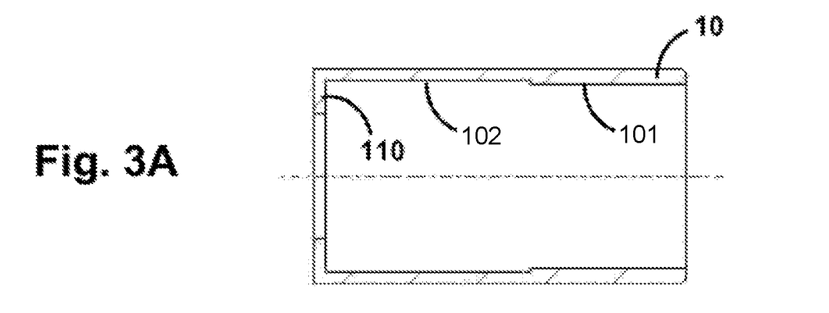
FIG. 3 shows schematic cross-sectional views of the sleeves according to numerous illustrative embodiments of the present invention.

A first illustrative embodiment of the present invention is described in detail below with reference to FIGS. 1 to 3. In particular, this illustrative embodiment is described with reference to FIGS. 1, 2A and 3A.

Figure 1A:
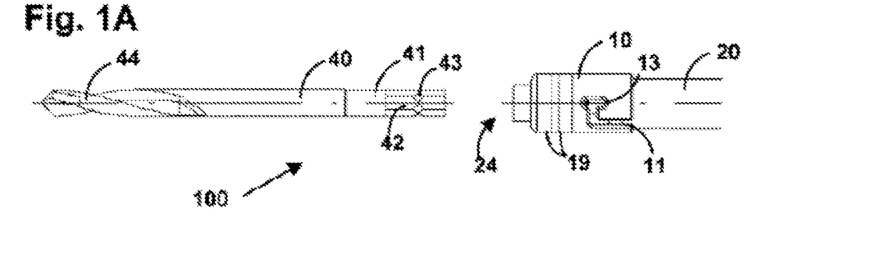
FIG. 1A shows a side view of a quick-action coupling according to the invention and of a suitable tool during the insertion of the tool into the quick-action coupling according to a first illustrative embodiment.
Figure 1B:
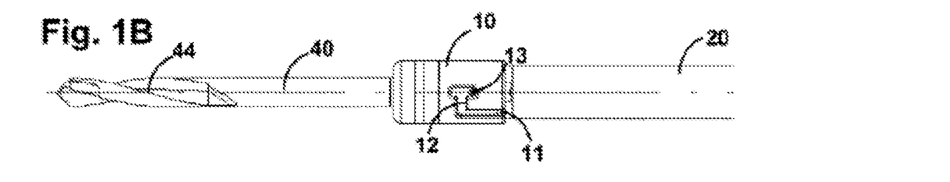
FIG. 1B shows a side view of a quick-action coupling according to FIG. 1A, in which a tool is locked.
Figure 1C:
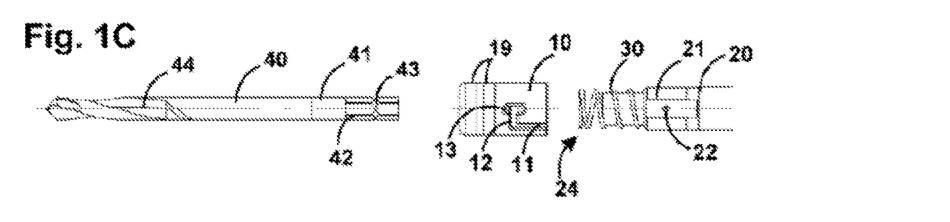
FIG. 1C shows a side view of a quick-action coupling according to FIG. 1A, wherein the quick-action coupling is dismantled.
Figure 1D:
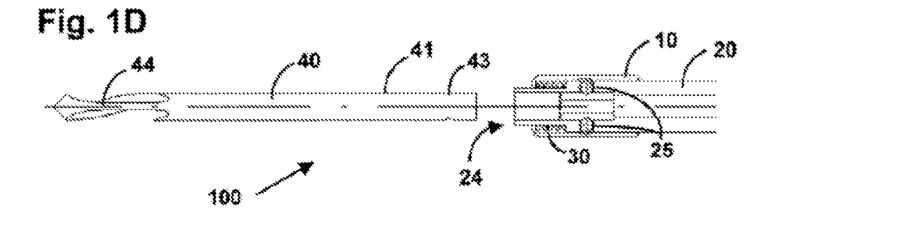
FIG. 1D shows a cross-sectional side view corresponding to FIG. 1A.
Figure 1E:
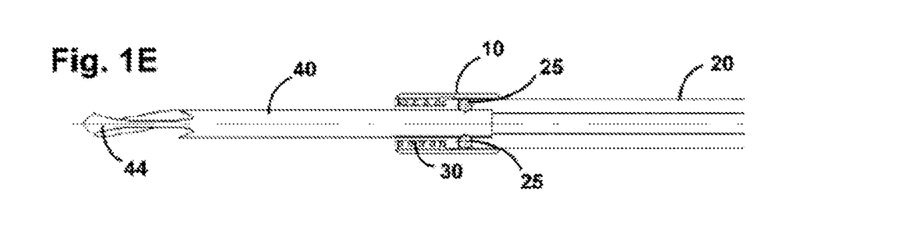
FIG. 1E shows a cross-sectional side view corresponding to FIG. 1B.
Figure 1F:
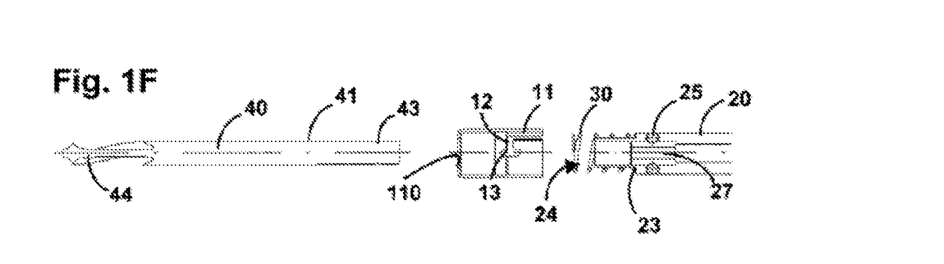
FIG. 1F shows a cross-sectional side view corresponding to FIG. 1C.

A quick-action coupling 100 according to the first illustrative embodiment has a rotary shaft 20, in the distal end surface of which there is formed a tool receptacle 24. The tool receptacle 24 receives the rear end 41 of a rotary surgical tool 40 for conjoint rotation therewith. For this purpose, the tool receptacle 24 is adapted to the hexagonal cross-sectional shape of the rear end 41 of the tool 40, as is shown in FIGS. 1A and 1C. The individual surfaces of the hexagonal tool receptacle 24 bear on the individual surfaces 42 of the rotary tool. The rotary shaft 20 has, in the area of its distal end 21, a radial projection 22 and two radial apertures, which apertures are not shown in FIGS. 1A to 1C. A ball 25 is arranged as a locking body in each of the two apertures, which balls are both movable in the radial direction with respect to the rotary shaft 20 and can thus enter the circumferential groove 43 in the rear end 41 of the tool 40 when the rear end 41 of the tool 40 is located in the tool receptacle 24.

The quick-action coupling 100 moreover has a sleeve 10, the proximal end of which is able to be pushed over the distal end 21 of the rotary shaft 20. The inner surface of the sleeve 10 has an area in which the internal diameter of the distal portion 102 is enlarged compared to the internal diameter of the proximal portion 101 by an individual step, as is shown in FIG. 3A. It will be seen from FIGS. 1D to 1F that the sleeve 10 has a substantially constant internal diameter. Only a circumferential groove on the inner surface of the sleeve generates the above-described step and thus also determines the defined area of the inner surface. The sleeve 10 moreover has a slot 11, 12, 13 which has a first slot portion 11, a second slot portion 12 and a third slot portion 13. In this illustrative embodiment, the slot is configured as a continuous slot. The first slot portion 11 extends from the proximal end of the sleeve 10. At the distal end of the first slot portion 11, the second slot portion 12 branches off in the radial direction and, at the other end of the latter, the third slot portion 13 is located, which extends away from the second slot portion 12 in the distal and proximal directions. The first and second slot portions 11, 12, and the second and third slot portions 12, 13, each form between them an angle α of 90°. A helical spring 30 urges the sleeve 10 in the distal direction relative to the rotary shaft 20. A bearing surface 23, 110 for the spring 30 is formed respectively on the sleeve 10 and on the rotary shaft 20, as can be seen from FIG. 1F.

To make the actuation of the sleeve 10 easier, two annular depressions 19 are provided on the outer surface thereof. The tool 40 shown in FIG. 1 is a twist drill with a hardened drill tip 44. This illustrative embodiment describes a quick-action coupling that is simple and convenient to produce, is easy to operate and can be dismantled and re-assembled quickly and in an uncomplicated way so as to ensure good cleaning and sterilization.

Figure 2A:
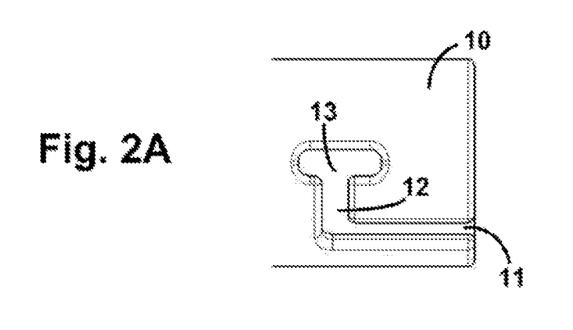
FIG. 2 shows schematic side views of a detail of the sleeves according to numerous illustrative embodiments of the present invention.
Figure 2B:
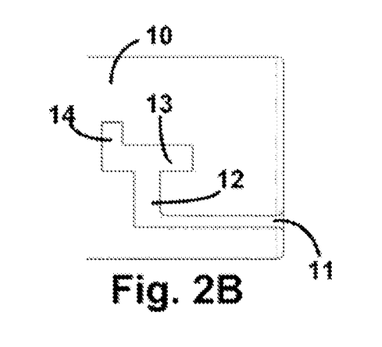
Figure 2C:
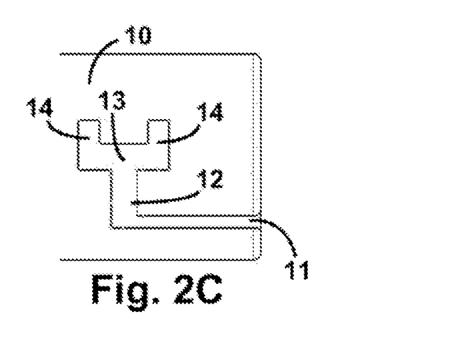
Figure 2D:
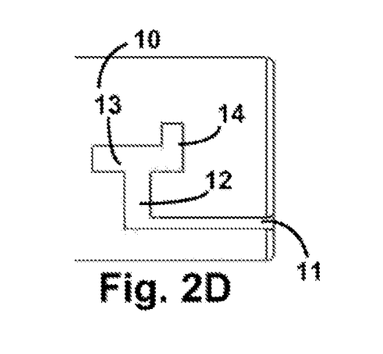
Figure 2E:
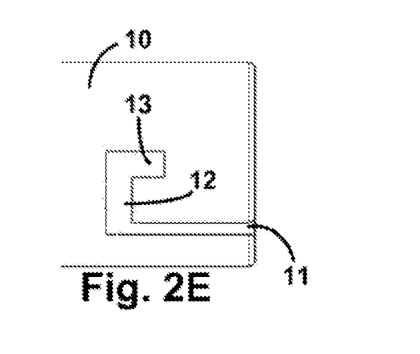
Figure 2F:
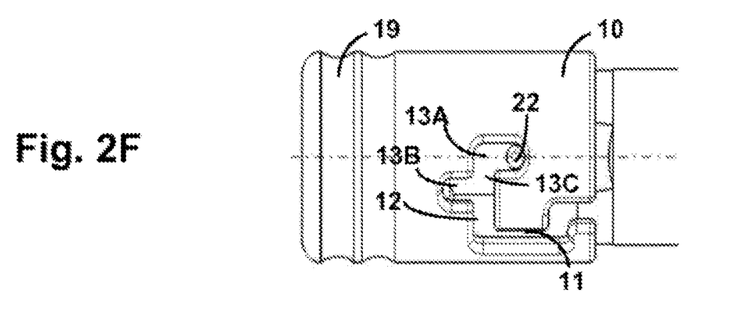
Figure 2G:
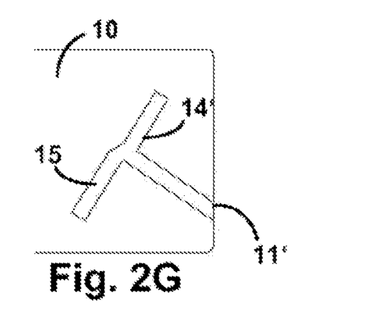
Figure 2H:
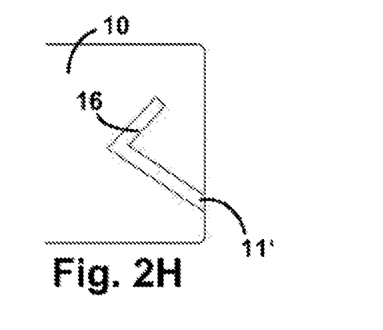
Figure 2J:
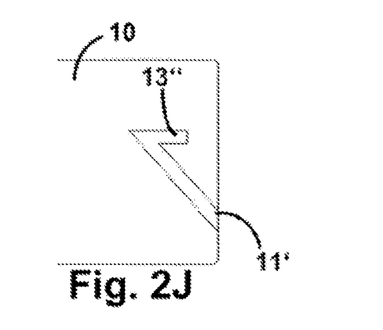
Figure 2K:
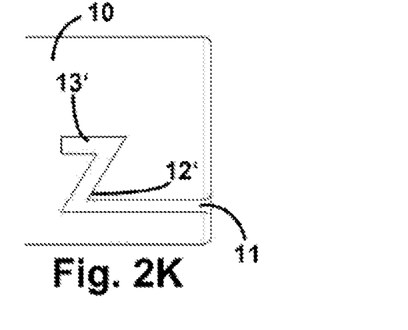

A particularly preferred second illustrative embodiment of the present invention is described in detail below with reference to FIGS. 1, 2F and 3B. The rotary shaft 20 of the second illustrative embodiment is identical to that of the first illustrative embodiment. Only the sleeve 10 differs from that of the first illustrative embodiment. To be precise, the only difference lies in the inner surface of the sleeve 10 and the shape of the slot 11, 12, 13.

Whereas the inner surface in the first illustrative embodiment is designed with a step between the two portions 101 and 102, in this illustrative embodiment an inclined surface 103 is provided between the two portions 101 and 102. The term inclined relates to the cross-sectional view in FIG. 3B. The inclined surface 103 is intended to ensure that the locking bodies, which are also balls in this illustrative embodiment, are urged more gently into the groove 43 in the tool 40. In this way, the sleeve 10 can be made slightly easier to handle, although this may also increase the necessary length of the sleeve 10, which in turn is undesirable.

Compared to the slot in the first illustrative embodiment, the slot in this illustrative embodiment is modified in two areas. On the one hand, the first slot portion 11 in this illustrative embodiment has a radial step 17 in order to prevent the sleeve from suddenly springing off the rotary shaft 20 during assembly or disassembly of the quick-action coupling. The radial step is formed by a procedure in which the first slot portion 11, which in this illustrative embodiment for the most part extends exactly in the distal direction, is provided with an area in which the slot 11 extends in the radial direction. To be precise, this portion even extends a little in the proximal direction. This means that the step 17 forms, on its distal side, a kind of niche in which the projection 22 can come to bear. If a slight pre-tensioning force is still applied to the sleeve 10 by the spring 30 in this position of the projection 22, this ensures that the projection 22 is secured as it were in this niche on the radial step 17.

On the other hand, the third slot portion 13 has a step-shaped configuration. That is to say, the area 13A of the third slot portion 13, which area extends in the proximal direction and is therefore the slot portion in which the tool 40 is optionally locked in the tool receptacle 24 of the rotary shaft 20, is radially offset in relation to the area of the third slot portion 13B, which area extends in the distal direction and is therefore the slot portion in which the tool 40 is optionally released in the tool receptacle 24. A radially extending area 13C is provided between the two portions 13A and 13B of the third slot portion 13. The area 13C is accordingly a continuation of the second slot portion 12.

Further illustrative embodiments of the present invention are shown in FIGS. 2 and 3. Numerous different shapes of a slot in the sleeve 10 are shown in FIG. 2. Of these, FIGS. 2A to 2E show further illustrative embodiments in which the adjoining slot portions always form between them an angle α of 90° and either extend in the radial or in the distal/proximal direction. FIGS. 2G and 2H show two further illustrative embodiments in which the slot portions all extend obliquely or diagonally. Moreover, in both cases, the angle α between the first slot portion 11' and the second slot portion 14, 15 or 16 is greater than 90°. FIGS. 2J and 2K show illustrative embodiments in which diagonal and distal/proximal slot portions are combined. Here too, the angles α formed between the slot portions are much greater than 90°. These figures are self-explanatory in light of the general description of the various required and optional tasks of the slot portions. In principle, it will merely be noted here that the reference signs 14 always designate portions that serve to secure the actual position of the sleeve 10 in the proximal/distal direction relative to the rotary shaft 20. Of course, the various slot portions of the different illustrative embodiments in FIG. 2 can also be suitably combined. For example, a radial slot portion 14 according to FIG. 2D can adjoin the proximal end of the slot portion 13 according to FIG. 2E in order to ensure that the sleeve is secured in the locking position. The same can also be provided in the illustrative embodiments of FIGS. 2G to 2J.

Figure 3B:
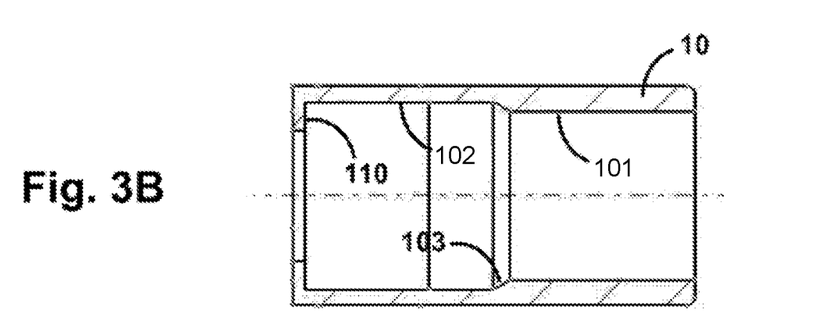
Figure 3C:
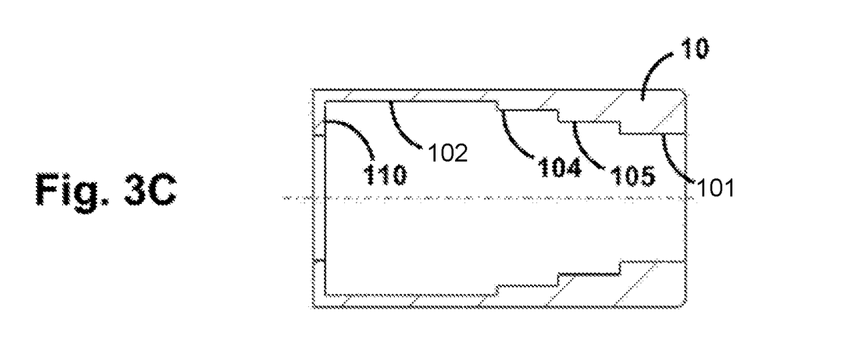

FIG. 3B shows a further structure of the inner surface of the sleeve 10. This inner surface has a multi-step design and thus represents an intermediate solution between the embodiments of FIGS. 3A and 3C. The intermediate steps 104 and 105 serve to subdivide the relatively large step between the portions 101 and 102. Depending on the machining method, it may be easier to configure a plurality of steps 101, 102, 104, 105 instead of an inclined surface 103, particularly since this inclined surface is curved in the direction of revolution of the sleeve 10.

Of course, all the embodiments of the inner surface of the sleeve 10 according to FIG. 3 can be combined in any desired manner with all the embodiments of the slots in the sleeve 10 according to FIG. 2. All of the other features that have been disclosed can likewise be suitably combined.

The invention claimed is:

1. A quick-action coupling for a rotary surgical tool comprising:
    a rotary shaft, in the distal end surface of which there is formed a tool receptacle which is configured to receive a rotary surgical tool for conjoint rotation therewith, wherein the rotary shaft has, in the area of its distal end, at least one radial projection and at least one radial aperture,
    a locking body is arranged in the at least one aperture, said locking body being movable in the radial direction with respect to the rotary shaft,
    a sleeve, the proximal end of which is able to be pushed over the distal end of the rotary shaft, wherein
    the inner surface of the sleeve has an area in which the internal diameter of the proximal portion is smaller than the internal diameter of the distal portion, and
    the sleeve has at least one slot which has a first slot portion and at least one further slot portion, wherein the first slot portion extends from the proximal end of the sleeve, and the further slot portion is connected to the first slot portion, and
    an elastic element which urges the sleeve in the distal direction relative to the rotary shaft.

2. The quick-action coupling as claimed in claim 1, wherein the elastic element is a helical spring which is arranged about the rotary shaft.

3. The quick-action coupling as claimed in claim 1, wherein a bearing surface for the elastic element is formed on the sleeve and/or on the rotary shaft.

4. The quick-action coupling as claimed in claim 1, wherein the locking body is a ball, and the aperture has, on both sides, a diameter that is smaller compared to a portion lying between said sides.

5. The quick-action coupling as claimed in claim 1, wherein the first slot portion extends substantially in the distal direction and, at its distal end, is connected to the second slot portion, which extends substantially in the radial direction.

6. The quick-action coupling as claimed in claim 5, wherein the first slot portion is connected via the second slot portion to a third slot portion, which extends from the second slot portion substantially in the distal and/or proximal direction.

7. The quick-action coupling as claimed in claim 1, wherein the first slot portion extends obliquely in the distal and radial direction and, at its distal end, is connected to the second slot portion.

8. The quick-action coupling as claimed in claim 7, wherein one end of the third slot portion is connected to a fourth slot portion, which extends substantially in the radial direction, wherein the other end of the third slot portion is connected to a fifth slot portion, which extends substantially in the radial or contra-radial direction.

9. The quick-action coupling as claimed in claim 7, wherein the second slot portion extends in the proximal direction and extends in the proximal and radial direction.

10. The quick-action coupling as claimed in claim 1, wherein a radial step is formed in the first slot portion, near the proximal edge of the sleeve.

11. The quick-action coupling as claimed in claim 1, wherein the slot portions can also have a bent or curved shape.

12. The quick-action coupling as claimed in claim 1, wherein two or three slots are provided which are arranged at uniform angular intervals along the circumferential direction of the sleeve, and wherein an equal number of radial projections are formed on the rotary shaft and are arranged correspondingly.

13. The quick-action coupling as claimed in claim 1, wherein two or three radial apertures are formed in the side wall of the tool receptacle and a ball is arranged as a locking body in each aperture, said ball being held in the aperture by means of at least one part of at least one edge of the aperture being plastically deformed toward the hole center.

14. The quick-action coupling as claimed in claim 1, wherein a step or an inclined surface is provided in the area of the inner surface of the sleeve between the proximal portion and the distal portion.

15. The quick-action coupling as claimed in claim 1, wherein the slot is configured in such a way that it extends through the entire wall thickness of the sleeve.

16. The quick-action coupling as claimed in claim 1, wherein the sleeve is movable distally from a release position to a locking position, the proximal end of the sleeve is pushed over the distal end of the rotary shaft as the sleeve moves between the release position and the locking position, the inner surface of the proximal portion of the sleeve urges the locking body toward the axis of the rotary shaft if the sleeve is in the locking position, and the inner surface of the distal portion of the sleeve permits radially outward movement of the locking body if the sleeve is in the release position.

17. The quick-action coupling as claimed in claim 16, wherein the sleeve remains connected to the rotary shaft when the sleeve is in the release position and when the sleeve is in the locking position.

\* \* \* \* \*